United States Patent [19]
Zajaczkowski

[11] Patent Number: 5,464,402
[45] Date of Patent: Nov. 7, 1995

[54] ABSORBENT GARMENT WITH CONFORMABLE PADS

[75] Inventor: Peter Zajaczkowski, Auburn, Wash.

[73] Assignee: Paragon Trade Brands, Inc., Federal Way, Wash.

[21] Appl. No.: 210,360

[22] Filed: Mar. 17, 1994

[51] Int. Cl.⁶ ..................................................... A61F 13/15
[52] U.S. Cl. ....................... 604/385.1; 604/378; 604/358
[58] Field of Search ...................................... 604/378, 385, 604/384, 358

[56] References Cited

U.S. PATENT DOCUMENTS

| 3,860,003 | 1/1975 | Buell . |
| 4,726,807 | 2/1988 | Young et al. . |
| 4,988,345 | 1/1991 | Reising . |
| 5,098,423 | 3/1992 | Pieniak et al. . |

FOREIGN PATENT DOCUMENTS

| 0410702 | 5/1934 | United Kingdom ................ 604/385.1 |
| WO91/09579 | 7/1991 | WIPO . |
| WO91/09580 | 7/1991 | WIPO . |
| WO91/09582 | 7/1991 | WIPO . |

Primary Examiner—Randall L. Green
Assistant Examiner—Rob Clarke
Attorney, Agent, or Firm—Klarquist Sparkman Campbell Leigh & Whinston

[57] ABSTRACT

An absorbent product having a backsheet, a liner sheet overlying the backsheet, and at least a pair of elongate absorbent pads mounted between the backsheet and liner sheet. The pads are disposed in an initial position with marginal side edge portions thereof disposed in a first overlap relationship and they are mounted in the product for shifting laterally relative to each other to vary the extent of overlap between the pads.

12 Claims, 1 Drawing Sheet

ABSORBENT GARMENT WITH CONFORMABLE PADS

BACKGROUND OF THE INVENTION

This invention relates generally to a disposable absorbent garment, such as a diaper or training pant, and more specifically to such a garment in which absorbent pads are laterally shiftable in the garment to conform to the wearer.

The primary function of disposable absorbent garments, such as disposable diapers, adult incontinent briefs, and training pants, is to absorb and contain excreted body fluids and other exudates. The typical disposable garment includes a layer of liquid retaining absorbent material sandwiched between a moisture pervious facing, or top sheet, layer positioned adjacent the skin of the wearer, and a moisture impervious backsheet to confine moisture within the absorbent layer.

In the past, the absorbent layer has typically been comprised of a pad, or bat, of loosely compacted absorbent fibers, usually comminuted wood pulp, or fluff. While such absorbent material is relatively inexpensive and capable of absorbing liquids, the typical absorbent garment including such material most generally is configured such that it detracts from the comfort of the wearer. Explaining further, prior disposable absorbent products generally have had an absorbent pad with defined side-to-side dimensions which provided little, if any, variability in width to conform to the wearer.

The effectiveness and comfort of an absorbent garment are directly related to the absorbent capacity of the pads and the manner in which they conform to the wearer's body.

With regard to wearer comfort, it will be recognized that a wearer generally has a relatively small distance between his or her upper thighs, and whatever width of diaper exists between the wearer's legs that is in excess of the wearer's natural crotch width, will necessarily produce potentially uncomfortable pressing against the wearer's thighs.

In the past, attempts have been made to overcome this problem by providing in-cut side leg regions in the pad in the crotch region of the garment. This, however, in a single layer absorbent pad merely diminishes the absorbent capability of the pad in the region in which high absorbent capacity is required.

Other attempts have been made previously to provide multi-layer pads, but these have generally set side-to-side dimensions in the crotch region, and thus do not easily conform to the size and configuration of the wearer. Such set side-to-side dimension pad configurations of prior devices also may be too narrow, so that they do not fit snugly in the wearer's crotch region and thus may not fit closely enough to the body to produce desired absorbent characteristics.

It is a general object of the present invention to provide a novel absorbent garment which has a pair of absorbent pads which are mounted in overlapping relationship and are shiftable laterally relative to each other to conform to the crotch region of the wearer to produce comfortable, yet effective, fit for the garment.

Another object of the invention is to provide an absorbent article having a first elongate absorbent pad, a second elongate absorbent pad, and a flexible sheet enclosure encasing the first and second pads, with the pads being disposed in an initial position laterally offset from each other, but with their adjacent edge margin portions overlapping such that the pads may shift laterally relative to each other from the initial overlap position to a second overlap position to vary the combined side-to-side dimension of the pads. This allows the pads to shift into varying degrees of overlap relationship to conform to the wearer's body, while still retaining adequate absorbent capacity in desired regions.

Yet another object of the present invention is to provide a novel garment which has a backsheet, a center pad secured to the backsheet along a central region thereof with side edge margin portions spaced outwardly from the region of connection to the backsheet free from the backsheet. A pair of elongate side pads also are secured to the backsheet in regions spaced outwardly from the securing of the center pad in the central region, with the side pads disposed in overlapping relationship with the side edge margins of the center pad. The opposed side edge margins of the center pad initially overlap the side pads by a distance which is a minor portion of a side-to-side dimension of the side pads. The cover sheets for the garment are sufficiently flexible that the side pads may shift laterally relative to the center pad to increase the overlap therebetween to an overlap dimension which may be a major portion of a side-to-side dimension of the side pad. With such construction a wide range of adjustability is provided for side-to-side dimension of the pads in the garment to produce a comfortable fit while maintaining adequate absorptive capacity.

In accordance with an embodiment of the present invention, an integral disposable absorbent garment is provided which includes a backsheet, a liner sheet overlying the backsheet, a first elongate absorbent pad positioned between the sheets, and a second elongate absorbent pad positioned between the sheets and offset laterally from the first pad, with the first and second pads being disposed in an initial position with marginal side edge portions thereof disposed in a first overlap relationship, and being mounted for shifting laterally relative to each other to vary the extent of overlap therebetween.

These and other objects and advantages will become more fully apparent as the following description is read in conjunction with the drawings.

DETAILED DESCRIPTION

Figure 1:
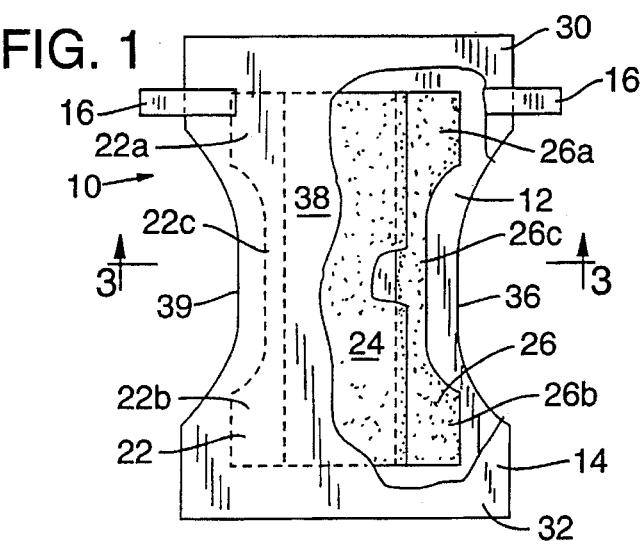
FIG. 1 is a plan view of a disposable absorbent garment according to an embodiment of the present invention having portions broken away to reveal underlying structure.

FIG. 1 illustrates a preferred embodiment of a disposable absorbent product 10 constructed in accordance with the invention having a liquid impervious outer layer, or backsheet, 12 and a liquid pervious body-contacting inner layer, topsheet, or liner sheet, 14. Tape tabs 16, 18 are secured to and extend laterally outwardly from one end portion of the garment and may be used to secure the garment on a wearer as is generally known.

Figure 2:
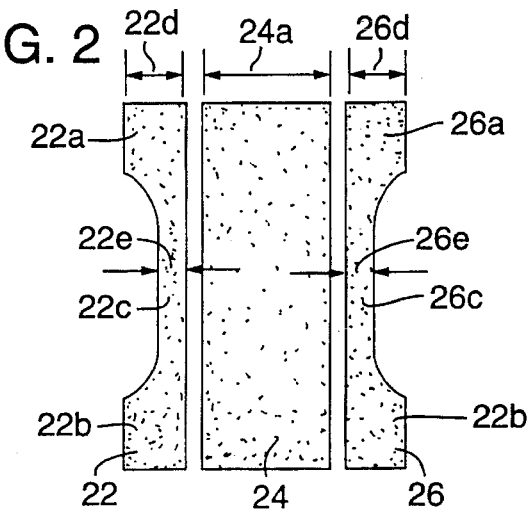
FIG. 2 is a plan view of three absorbent pads used in the garment of FIG. 1.

Referring to FIG. 2, three elongate absorbent pads 22, 24, 26 are illustrated. Pad 24 is substantially rectangular, having a width denoted at 26a.

Pads 22, 26 are substantially mirror images of each other. Pad 22 has opposed end portions 22a, 22b which have a side-to-side dimension indicated generally at 22d, and an in-cut side leg portion forming a crotch region 26c having at its center a width 22e which is less than 22d. Similarly, pad 26 has opposed end portions 26a, 26b having a width 26d, and an in-cut side leg portion forming a crotch region 26c having a side-to-side dimension 26e which is less than dimension 26d.

Absorbent pads 22, 24, 26 may be made of wood fibers, or other fibers, such as chemical wood pulp, or any other suitable liquid absorbing material such as commercially available fluff pulp or fluff bleached craft soft wood pulp. The pads may have a superabsorbent material distributed therein for enhancing the liquid absorbing capability of the pads.

The disposable absorbent garment as illustrated at 10 typically is such as would be used as a baby or infant diaper, or as an adult incontinent brief. Other uses for a product according to this invention, but having a different outline configuration, would be for use as a sanitary napkin, or other absorbent products.

The general manufacture of such garments, or products, is well-known in the art. One method of manufacture is illustrated in U.S. Pat. No. 4,726,807 to Richard H. Young and Peter Lancaster, which is herein incorporated by reference to illustrate typical materials used and methods of manufacturing such garments. Such referenced patent is for general information only and is not meant to limit the scope or disclosure of the present invention.

In the present example the liquid impervious backsheet 12 may be formed of a thin thermoplastic material, such as a pigmented polyethylene film having a thickness in the range of 0.02 to 0.04 mm. The liquid pervious liner sheet 14 may be any suitable material known in the art. By way of example only, sheet 14 may be a carded thermobonded polypropylene fabric, or a carded polyester fiber with a latex binder. Another suitable material might be a spun-bonded polypropylene having continuous fibers and thermally bonded by patterned calendar rollers. The liner sheet may be impregnated with a surfactant to render it hydrophilic. Pads 22, 24, 26 may be made from any suitable absorbent material, including cellulosic fibers or other absorbent fibers, and including chemical wood pulp, and non-cellulosic materials such as polyester or nylon fibers. As is well known in the art, superabsorbent material may also be dispersed into the pad. Such superabsorbent material generally is a water insoluble, but water-swellable, polymeric substance capable of absorbing liquid in an amount that is at least 10 times the weight of the polymeric substance in its dry form. The superabsorbent material can be in the form of particles, fibers, spheres, bits of film, globules, or the like.

The garment has opposed transverse waist regions 30, 32 disposed to lie along the front and rear waist areas of a wearer. Opposed in-cut side margins 34, 36 provide a somewhat hourglass shape to the garment. When the garment is fitted on a wearer, the opposed side margins 34, 36 define leg-encircling openings, waist region 30 contacts the rear waist area of the user, and waist region 32 contacts the wearer's front waist region. Lying between the opposed side margins 34, 36 and waist regions 30, 32 is a crotch region 38 which is substantially central to the garment.

Figure 3:
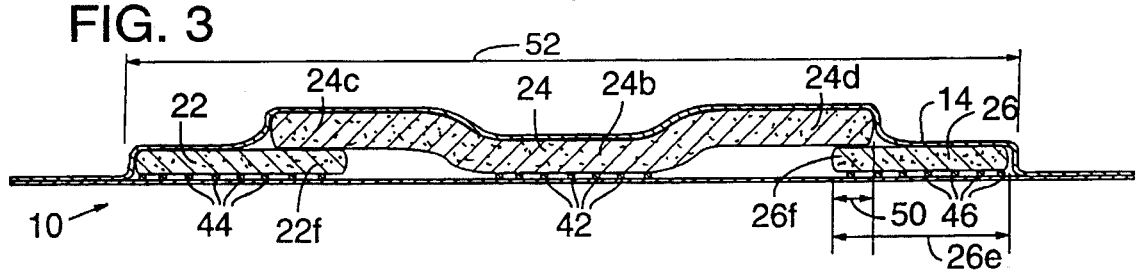
FIG. 3 is an enlarged cross-sectional view taken generally along the line 3—3 in FIG. 1 illustrating an assembled garment with side edge margin portions of pads within the structure in an initial overlap position.

Referring to FIGS. 1 and 3, the garment is constructed with pad 24, also referred to herein as the center pad, extending longitudinally of the central portion of the garment. As illustrated in FIG. 3, pad 24 is secured along its central region 24b to the longitudinal center region of backsheet 12 by a plurality of strips of adhesive indicated generally at 42. Opposed side edge margins 24c, 24d of the center pad are free of securement to the backsheet.

Absorbent pads 22, 26, also referred to herein as side pads, are secured to backsheet 12 by strips of adhesive material 44, 46 in regions spaced from the center region where the center pad is adhered to the backsheet.

Side edge margins 22f, 26f of the side pads underlie and are overlapped by side edge margins 24c, 24d of the center pad, respectively. In the drawings some space has been provided between the elements for purposes of clarity. In reality the pads and liner sheet would rest against each other. Upon initial construction of the garment the initial overlap between the side edge margins is as indicated at 50 wherein it is noted that the extent of overlap between side edge margin 24d and side edge margin 26f is a minor portion of the width of a side-to-side dimension 26e of side pad 26. The extent of overlap between side edge margins 24c and 22f at the opposite side of the garment similarly is a dimension which is a minor portion of a side-to-side dimension of side pad 22.

With the absorbent pads secured to backsheet 12, the outer peripheral edge margins of the liner sheet and backsheet are secured together, as by known adhesive, or bonding, processes to encase the absorbent pads therebetween.

In the structure as initially produced as shown in FIG. 3, a side-to-side dimension of the combined side pads 22, 26 and center pad 24 is indicated at 52. This is the side-to-side dimension between outer side edges of the crotch portions 22c, 26c, of side pads 22, 26.

Figure 4:
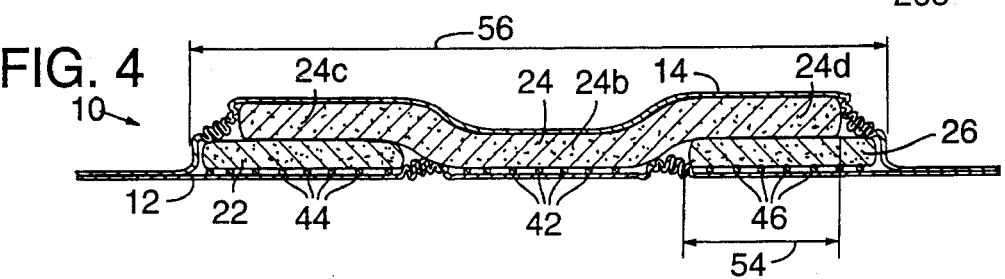
FIG. 4 is a cross-sectional view similar to that of FIG. 3, but with the absorbent pads shifted laterally to a second overlap position in which the extent of overlap between side edge margins of the pads is increased.

As is illustrated in FIG. 4, the structure thus described, due to the flexibility of liner sheet 14 and backsheet 12, permits lateral shifting of side pads 22, 26 under side edge margins of the center pad 24 to vary the side-to-side dimension of the combined set of pads. The side pads are unconnected to liner sheet 14, such that they are permitted to shift transversely inwardly toward the center of the garment to the position illustrated in FIG. 4. In FIG. 4 the pads are illustrated shifted to positions wherein the overlap between side edge margins of the center pad and a side pad may be a distance which is a major portion of a side-to-side dimension of a side pad, as indicated generally at 54 for side pad 26. This permits a side-to-side dimension of the combined set of absorbent pads in the garment to contract to a dimension 56 as illustrated in FIG. 4 which is less than side-to-side dimension 52 for the initial position of the pads illustrated in FIG. 3.

As is seen in FIGS. 3 and 4, the undersides of the marginal side edge portions of the center pad 24 and the upper surfaces of the side pads 22, 26 which define facing surfaces in the structure are substantially/planar as viewed in cross-section. This permits the side pads to shift laterally relative to the center pad to vary the overlap therebetween, without significantly varying the combined thickness of the overlapping portions.

In FIG. 1, a disposable diaper 10 is shown generally in position for fitting to a wearer with the absorbent pads in the initial disposition illustrated in FIG. 3. With the diaper positioned as shown, a baby may be placed face up on the diaper. The forward portion of the diaper bearing waist portion 32 is brought up between the baby's legs to a position contiguous with the front portion of the baby's waist. The diaper thereafter is secured to the baby by bringing end portions of the rear waist region 30 around the baby into overlapping relation with front waist portion 32, and tabs 16, 18 are adhesively connected to waist region 32 to secure the diaper on the baby.

As the diaper is fitted on the child the side pads 22, 26 may shift inwardly under center pad 24 toward the position illustrated in FIG. 4 to conform, in the child's crotch region, to the narrower space between the inner sides of the baby's legs. Due to the inherent flexibility of the pads remainder portions of the side pads spaced toward end portions 22a, 22b and 26a, 26b may remain more nearly in the initial position with a minor degree of overlap with the side margins of the center pad.

The side pads thus shift laterally as needed to provide comfortable conformity with the crotch region of the wearer, yet continue to provide effective fit and adequate receiving capacity.

The method for manufacturing such a garment generally follows previous manufacturing techniques. First, a backsheet 12 is formed, and strips of longitudinally extending adhesives 42, 44, 46 are laid on the backsheet in the positions illustrated in FIG. 3. Absorbent pads 22, 26 are placed on the backsheet over their respective strips of adhesive materials 44, 46 and thus secured to the backsheet. Center pad 24 is placed on the backsheet with its central region 24b secured thereto by adhesive strips 42. The outer side edge marginal portions 24c, 24d overlie side margin portions 22f, 26f of the side pads. A liner sheet 14 is formed and is laid over the absorbent pads and the backsheet. The outer peripheral edge margins of backsheet 12 and liner sheet 14 are adhered together by adhesives or other known joining methods to form a flexible encasing structure within which the absorbent pads are mounted. The garment may be formed initially with straight sides on the liner and backsheet and the incut leg regions 34, 36 may be produced after the liner and back sheets are joined. Adhesive tabs 16, 18 then are attached to the structure.

A garment thus is formed which, in its initial configuration, has elongate absorbent side pads which have only a minor degree of overlap with marginal side edge portions of the center pad. However, when the garment is placed on a wearer the side pads may shift transversely as needed to allow the overall crotch region of the garment to vary its side-to-side dimension as the side sections slide under the center section. In this way the effective width of the crotch section of the pad is adapted to conform to and fit comfortably in the crotch region of a wearer without losing absorbent capacity and without reducing the effective leakage performance of the garment.

While a preferred embodiment of the invention has been described herein, it should be recognized that variations and modifications are possible without departing from the spirit of the invention which is set out in the following claims.

I claim:

1. An absorbent garment comprising a back sheet, a liner sheet overlying said back sheet, a first elongate absorbent pad positioned between said sheets and having a longitudinal center region, and a second elongate absorbent pad positioned between said sheets offset laterally from the center region of said first pad, said first and second pads being disposed in an initial position with marginal side edge portions thereof disposed in a first overlap relationship and being mounted in said garment for shifting laterally relative to each other to vary the extent of overlap therebetween, said first and second pads having substantially planar facing surfaces permitting varying said overlap without significantly varying the combined thickness of said overlapping portions.

2. The garment of claim 1, wherein the first overlap between said pads is a minor portion of a side-to-side dimension of one of said pads and said pads are shiftable to a second position wherein the overlap between said pads is a major portion of said side-to-side dimension of said one pad.

3. An absorbent garment comprising a back sheet, a liner sheet overlying said back sheet, a first elongate absorbent pad positioned between said sheets and having a longitudinal center region, and a second elongate absorbent pad positioned between said sheets offset laterally from the center region of said first pad, said first and second pads being disposed in an initial position with marginal side edge portions thereof disposed in a first overlap relationship and being mounted in said garment for shifting laterally relative to each other to vary the extent of overlap therebetween, wherein the first overlap between said pads is a minor portion of a side-to-side dimension of one of said pads and said pads are shiftable to a second position wherein the overlap between said pads is a major portion of said side-to-side dimension of said one pad, and said first pad is secured to one of said sheets in a first region spaced from the region of overlap between said first and second pads, said second pad is secured to one of said sheets in a second region spaced from said first region and said sheets are sufficiently flexible to permit said first and seconds pads to shift laterally relative to each other between said initial and second positions.

4. The garment of claim 3, wherein said first pad is secured to said back sheet, and said second pad is positioned between said first pad and said backsheet.

5. The garment of claim 3, wherein said first pad is in contact with said one sheet in said first region, the marginal edge portion of said first pad is spaced from said sheet, and the second pad is interposed between said sheet and said marginal edge portion of said first pad.

6. The garment of claim 5, wherein said first pad and said second pad are secured to the same sheet.

7. An absorbent garment comprising a back sheet, a liner sheet overlying said back sheet, a first elongate absorbent pad positioned between said sheets and having a longitudinal center region, and a second elongate absorbent pad positioned between said sheets offset laterally from the center region of said first pad, said first and second pads being disposed in an initial position with marginal side edge portions thereof disposed in a first overlap relationship and being mounted in said garment for shifting laterally relative to each other to vary the extent of overlap therebetween, and said first and second pads are secured to said back sheet at laterally spaced regions of the backsheet and an expanse of said backsheet extends between said regions to which the pads are secured, said expanse of backsheet being sufficiently flexible to permit said first and second pads to shift laterally relative to each other to increase the extent of overlap therebetween.

8. The garment of claim 7, wherein said second pad is free from connection to said liner sheet.

9. An absorbent garment comprising a back sheet, a liner sheet overlying said back sheet, a first elongate absorbent pad positioned between said sheets and having a longitudinal center region, and a second elongate absorbent pad positioned between said sheets offset laterally from the center region of said first pad, said first and second pads being disposed in an initial position with marginal side edge portions thereof disposed in a first overlap relationship and being mounted in said garment for shifting laterally relative to each other to vary the extent of overlap therebetween, wherein one of said pads has a incut leg portion defining a side edge of a crotch region for said one pad, and wherein the first overlap between said pads is a minor portion of the side-to-side dimension of the crotch region of said one pad, and said pads are shiftable to a second position wherein the overlap between said pads is a major portion of said side-to-side dimension of said crotch region.

10. An absorbent article comprising a first elongate absorbent pad having opposed side edge margin portions and a longitudinal center region, a second elongate absorbent pad having opposed side edge margin portions, and a flexible sheet enclosure encasing said first and second pads, said pads being disposed in an initial position contiguous each other and with the second pad laterally offset from the longitudinal center of the first pad in said sheet enclosure to define a first combined side-to-side dimension with adjacent side edge margin portions thereof overlapping, said pads mounted in said enclosure for shifting laterally relative to each other from said initial position to a second position to vary the overlap between the pads to vary the combined side-to-side dimension of said pads, said first and second pads having substantially planar facing surfaces permitting varying said overlap without significantly varying the combined thickness of said overlapping portions.

11. An absorbent garment comprising a back sheet, a liner sheet overlying said back sheet, an elongate absorbent center pad having opposed side edge margins positioned between said sheets and extending longitudinally thereof, a first elongate absorbent side pad positioned between said sheets and extending along one side of said center pad with adjacent side edge margin portions of said center pad and first pad overlapping, and a second elongate absorbent side pad positioned between said sheets and extending along the side of said center pad opposite said one side with adjacent side edge margin portions of said center pad and second pad overlapping, said pads when in a first position having a first side-to-side width for the combined set of pads and being shiftable laterally relative to each other to vary the extent of overlap therebetween and the side-to-side width of the combined set of pads, said pads having substantially planar facing surfaces permitting varying said overlap without significantly varying the combined thickness of said overlapping portions.

12. An absorbent garment comprising a back sheet, a liner sheet overlying said back sheet, an elongate absorbent center pad positioned between said sheets and secured to one of said sheets along its center region with opposed marginal edge portions of said center pad free from connection to said sheet, a first elongate absorbent side pad positioned between said sheets offset laterally from the center region of said center pad toward one side of the center pad, a second elongate absorbent side pad positioned between said sheets offset laterally from the center region of said center pad to the opposite side of the center pad from said first side pad, said first and second side pads being disposed in an initial position with marginal side edge portions thereof disposed in a first overlap relationship with opposed marginal edge portions of the center pad and being mounted in said garment for shifting laterally relative to the center pad to vary the extent of overlap therebetween, said side pads being secured to one sheet in regions spaced from said center region, with flexible portions of said sheet extending between said regions allowing the side pads to shift laterally under the opposed marginal edge portions of the center pad.

* * * * *